United States Patent [19]

Byers

[11] Patent Number: 4,645,504

[45] Date of Patent: Feb. 24, 1987

[54] IMPLANTABLE INFECTION BARRIER SEAL AND METHOD

[75] Inventor: Charles L. Byers, Vacaville, Calif.

[73] Assignee: The Regents of the University of California, Berkeley, Calif.

[21] Appl. No.: 738,021

[22] Filed: May 24, 1985

[51] Int. Cl.[4] .............................................. A61F 2/18
[52] U.S. Cl. ...................................... 623/10; 623/66; 623/11; 623/12; 623/16; 128/92 YQ; 604/174; 604/175
[58] Field of Search ..................................... 623/10–12, 623/16, 66; 128/92 G, 92 C, 1 R; 604/175, 174

[56] References Cited

U.S. PATENT DOCUMENTS 3,663,965 5/1972 Lee, Jr. et al. ......................... 623/11

FOREIGN PATENT DOCUMENTS 0002068 5/1979 European Pat. Off. .............. 623/10

Primary Examiner—Richard J. Apley
Assistant Examiner—Gregory Beaucage
Attorney, Agent, or Firm—Phillips, Moore, Lempio & Finley

[57] ABSTRACT

An implantable infection barrier seal for preventing the entry of pathogens into an anatomical body, the body defining an exterior where pathogens reside and an interior where pathogens are not endemic. The body interior includes organic tissues which are not inherently exposed to the exterior. A portion of the tissue is exposed to the exterior. The seal includes an implantable infection barrier member that comprises of an inert, biologically compatible material which is bonded to the exposed tissue portion so as to shield the body interior from the pathogens residing in the exterior.

31 Claims, 3 Drawing Figures

IMPLANTABLE INFECTION BARRIER SEAL AND METHOD

TECHNICAL FIELD

This invention relates to implantable prostheses, and more particularly, to an implantable infection barrier seal.

BACKGROUND ART

With the advent of implantable prostheses, a new type of infection is becoming prevalent. That new type of infection is generally categorized as prostheses-enhanced infection, i.e., infection enhanced by the presence of such implantable prostheses. Since most implantable prostheses are manufactured from materials which living tissue does not bond to, a fibrous lining or sheath of connective tissue invariably forms around such an implant. In addition, many implantations require the piercing of the epithelium layer, the anatomical bacterial barrier or shield. Coupled with the piercing of the epithelium, the fibrous sheath or lining, which does not adhere to the implant, tends to leave an open channel between the implant and itself, an ideal pathway for invading pathogens. To prevent any potential infection, antibiotics must be used. In many instances, however, continuing use of antibiotics may be impractical or impossible after the original application of such antibiotics. For example, antibiotics are generally used at the initial implant stages of implanting an intracochlear device. After such a device is in position, application of such antibiotics is not practical, e.g., applying antibotics to the middle ear region. Moreover, continued chronic use of antibiotics may be undesirable. Further, once infection has set in around a foreign body such as an implant, antibiotics are ineffective in combatting the infection since the infection will remain chronic until the foreign body is removed. An implantable infection barrier seal is, therefore, desirable.

The ideal implantable infection barrier seal should be capable of providing a permanent barrier to infectious pathogens. It should be capable of eliminating passageways for such pathogens. In addition, such an implantable seal should be capable of minimizing or eliminating the need for the continued use of antibiotics.

DISCLOSURE OF THE INVENTION

In view of the prior art, it is a major object of the present invention to provide an implantable infection barrier seal that forms a barrier against invading pathogens such as the elimination of passageways for such pathogens.

It is another object of the present invention to provide an implantable infection barrier seal that minimizes or eliminates the necessity of using antibiotics.

It is a further object of the present invention to provide an implantable infection barrier seal that is capable of functioning as an anchor for a prothesis such that the prothesis is not easily dislodged when such dislodgment could compromise the effectiveness of the prothesis or promote the entry of pathogens.

In order to accomplish the above and still further objects, the present invention provides an implantable infection barrier seal for preventing the entry of pathogens into an anatomical body, the body defining an exterior where pathogens reside and an interior where pathogens are not endemic. The body interior includes organic tissues which are not inherently exposed to the exterior. A portion of the tissues is exposed to the exterior. The seal includes an implantable infection barrier member that comprises an inert, biologically compatible material which is bonded to the exposed tissue portion so as to shield the body interior from the pathogens residing in the exterior.

Other objects, features and advantages of the present invention will appear from the following detailed description of the best mode of a preferred embodiment, taken together with the accompanying drawings.

BEST MODE FOR CARRYING OUT THE INVENTION

Figure 1:
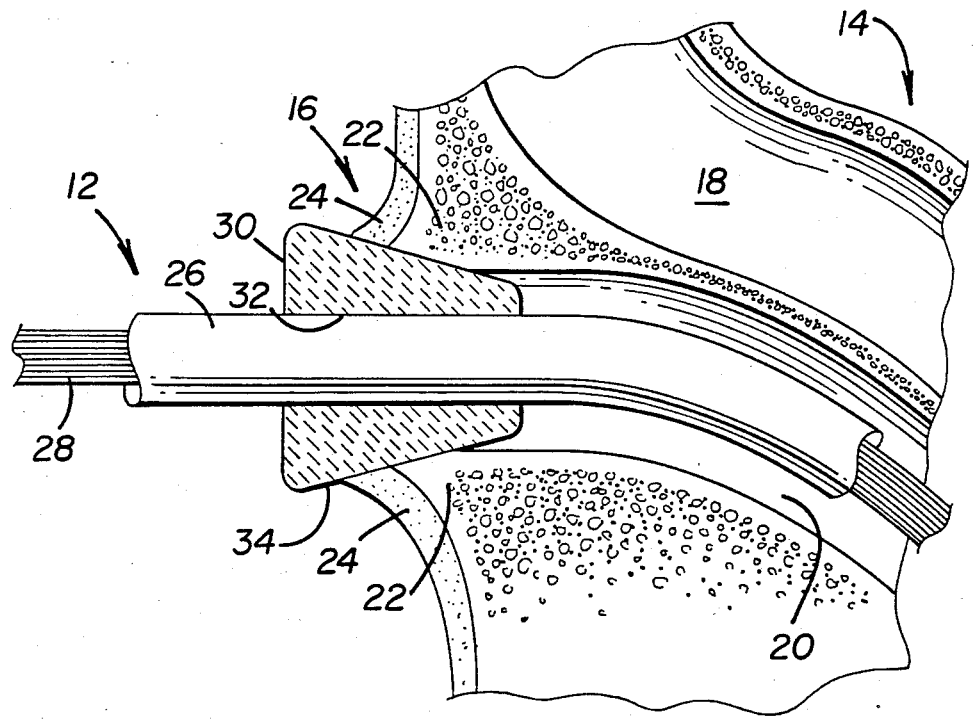
FIG. 1 is a partial, enlarged cross section view of the implantable infection barrier seal of the present invention.

Referring to FIG. 1, there is shown an implantable prosthesis, designated 12. In this particular instance, prosthesis 12 is an intracochlear device that is implanted within a cochlea 14. As illustrated, cochlea 14 has a round window 16, scala vestibuli 18 and scala tympani 20. Round window 16 is a bony opening 22 with an epithelium layer 24. Intracochlear device 12 has a tubular member 26 that envelops a bundle of elongated electrode wires 28. Intracochlear device 12 enters cochlea 14 at its round window 16. Since intracochlear device 12 is manufactured from a material that is foreign, albeit inert, to the cochlear tissues, a fibrous lining or sheath invariably grows and envelops device 12, not shown. The phenomenon of fibrous growth around a foreign object is well within the knowledge of one skilled in the art. Since the fibrous sheath does not bond with device 12, a passageway or channel develops between it and device 12, also not shown. The resulting passageway between device 12 and the sheath is an ideal conduit for the entry of pathogens from the exterior of the body. Although the intracochlear device 12 is implanted with a topical application of antibiotics, it is not possible to apply additional antibiotics after the implantation. Thus, developing a middle ear infection is possible in anyone, especially children. Middle ear infections could evolve into dangerous, and even life-threatening infections, since the cochlea is in direct communication with the brain and the central nervous system.

Accordingly, an implantable infection barrier seal of the present invention is provided, generally designated 30. Infection seal 30 is manufactured from an inert, biologically compatible material, a ceramic material in the preferred embodiment. The ceramic material of the preferred embodiment, an osteogenesis compatible material, is calcium hydroxy-apatite, marketed under the trademark CERAVITAL, registered to Xomed, Inc. of Florida. Seal 30 in the preferred embodiment is a porous material that is capable of bonding with connective tissues, especially osteogenic tissue. The pore size of the material should be of a range from 50 to 400 micrometers.

More particularly, infection seal 30 in the preferred embodiment is an annular device that is mounted on intracochlear device 12. An inner perimeter 32 of annular seal 30 is bonded to the polymeric tubular body 26 of intracochlear device 12. An outer perimeter 34 of annular seal 30 is in turn placed contiguous to bone 22 of round window 16. Since the material of annular seal 30 is compatible with bone 22 of round window 16, annular device 30 quickly receives new growth of bone 22 and bonds therewith. In addition, epilithium 24 also grows onto annular seal 30 and develops a fibrous tissue bond. Such bonding eliminates potential pathogen passageways between intracochlear device 12 and bone 22 of round window 16.

In addition to the prevention of infection, annular device 30 in this embodiment provides a mechanical support or anchor for intracochlear device 12. Whereas prior art intracochlear devices are not anchored, resulting in slippage and movement, intracochlear device 12 in the preferred embodiment is secured to bone 22 of round window 16 by annular seal 30. Dislodgment of device 12 such as slippage and movement could reduce the prosthetic value of such an implant. In addition, dislodgment of device 12 could open a passageway such that external pathogens could enter into the interior of the body.

In use, a conventional intracochlear device 12 is selected. Device 12 has a length of approximately 70 millimeters, with a 25-millimeter portion of which is disposed inside cochlea 14, and a diameter of approximately one millimeter. The bundle of electrode wires 28 is encased within elongated tube 26 which is manufactured from a silicon elastomer, generally referred to as silastic. An annular implantable inflection barrier seal 30 is then selected. Seal 30 in the preferred embodiment has dimensions which are appropriate for the application. Inner perimeter 32 of seal 30 is first conventionally bonded to silastic casing 26 of intracochlear device 12. A conventional silastic adhesive is used for this purpose. For bonding annular seal 30 to round window 16, portions of round window 16 are removed to expose bony portion 22. A membrane, not shown, that covers the opening of round window 16 is removed. In addition, appropriate portions of epithelium layer 24 are either removed or opened. Portions of infection seal 30 adjacent its outer perimeter 34 are placed contiguous to bone 22 of round window 16. This procedure is a conventional technique readily known to one skilled in the art. Thus positioned, the pores of seal 30, generally in the range of 50 to 400 micrometers in the preferred embodiment, permit the growth of bone tissues thereon, producing a permanent bond between seal 30 and bone 22 of round window 16. In addition, epithelium 24 also forms bonds with annular seal 30. The resultant permanent bond, thereby, eliminates the possibility of passageways which may enhance the entry of pathogens from the exterior of the body. Moreover, the particular use of seal 30 in the preferred embodiment creates an anchor for intracochlear device 12 such that slippage and movement of device 12 is minimized or eliminated.

Figure 2:
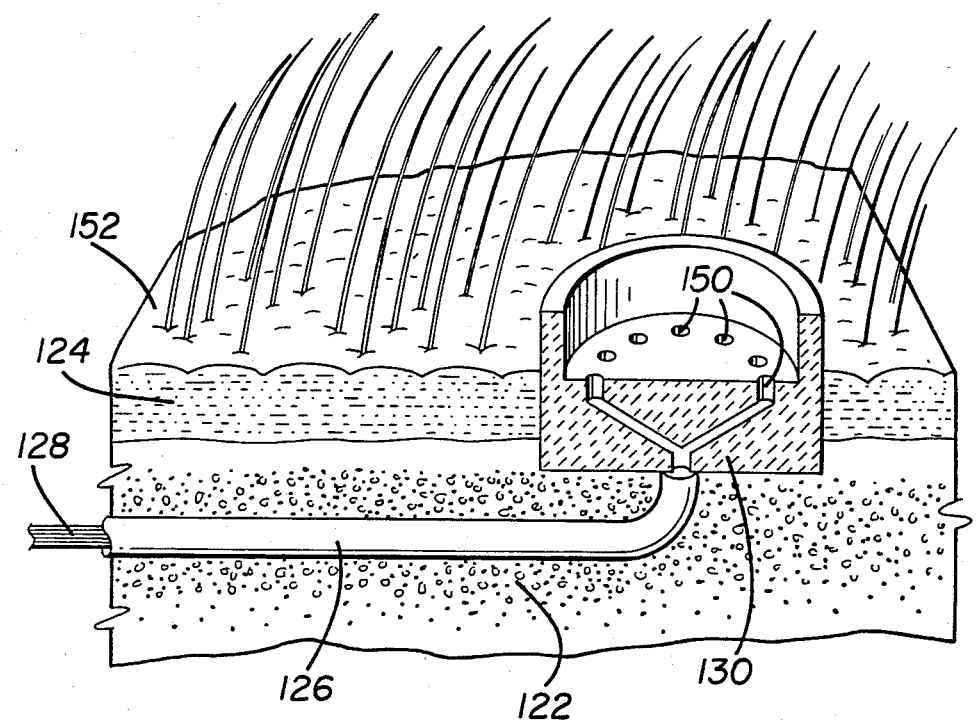
FIG. 2 is a partial, enlarged cross section view of another embodiment of the implantable infection barrier seal of the present invention.

As best shown in FIG. 2, an alternative embodiment of infection seal 30 is illustrated. In this embodiment, an implantable infection barrier seal 130 is provided. Since many elements in the alternative embodiment are similar to elements of the preferred embodiment, a numeral "1" is added to the numerals which designated corresponding elements of the preferred embodiment. For example, the infection seal of the alternative embodiment is designated 130.

Infection seal 130 in the alternative embodiment is configured as a tissue-integrated percutaneous connector. Such a connector is generally implanted in order to provide means to activate instruments and devices which are implanted deeper inside a body. Thus, a plurality of electrical connecting ports 150 are provided which in turn are connected to a plurality of electrical wires 128. Electrical wires 128, connected to an implanted device, not shown, is encased with tubular cable 126.

In use, an appropriate amount of bone 122 is removed such that seal 130 may be placed therein. In addition, an appropriate conduit is formed such that it is capable of receiving cable 126. In due course, bonding would occur between seal 130 and bone 122 and between seal 130 and epithelium layer 124. The external portion of epithelium 124, generally referred to as skin, is designated 152. Whereas prior art implants could not form a seal between an implant and the bone, pathogens from the exterior would likely to travel between the implant and the bone such that infections would occur. Even more invidious is when pathogens would travel along the conduit of cable 126 and infect an internal region deep within the body.

Figure 3:
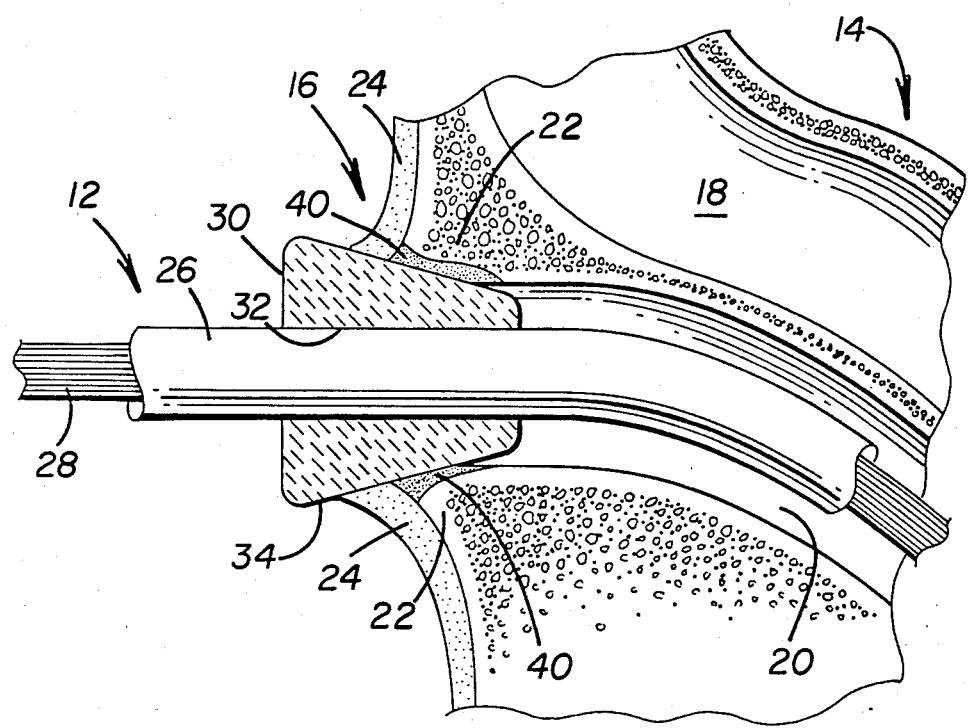
FIG. 3 is a partial, enlarged cross section view of a further embodiment of the implantable infection barrier seal of FIG. 1.

FIG. 3 illustrates a further alternative embodiment in which a paste-like composition 40 of autologous bone chips is positioned at the junction between seal 30 and bone 22 of round window 16. Composition 40 is generally referred to as pate. Pate 40 enhances the bonding of seal 30 with bone 22. This procedure is generally necessary to fill any gap that may exist between bone 22 and an implant since it is generally difficult to provide a site on bone 22 that exactly matches the dimensions of an implant. In addition, pate 40 may be used at a site on the body where bone is required, but absent. Thus, pate 40 is used to provide the growth of a bony site. These procedures are also conventional techniques readily known to one skilled in the art. Although bone 22 and pate 40 are illustrated as two separate entities, they will eventually evolve into a single entity, bone 22, after the bone chips of pate 40 grow into and merge with bone 22.

It will be apparent to those skilled in the art that various modifications may be made within the spirit of the invention and the scope of the appended claims. For example, although only connective tissues such as bone and epithelium have been described, the human body nonetheless includes other tissues positioned adjacent to or interlaid between these enumerated tissues and those other tissues may bond with the infection seal.

I claim:

1. An implantable infection barrier seal for preventing the entry of pathogens into an anatomical body, said body defining an exterior where pathogens reside and an interior where pathogens are not endemic, said body interior including organic tissues, defining an opening, which are not inherently exposed to said exterior, a portion of said tissues being exposed to said exterior, comprising an implantable infection barrier member shaped to fit within said opening and comprising an inert, biologically compatible material that is capable of being bonded directly to said exposed tissue portion so as to shield said body interior from said pathogens residing in said exterior, wherein said implantable infection barrier member comprises a porous ceramic material having a pore size in the range of form 50 to 400 micrometers.

2. The implantable infection barrier seal as claimed in claim 1, wherein said implantable infection barrier member comprises an osteogenesis compatible material.

3. The implantable infection barrier seal as claimed in claim 1, wherein said implantable infection barrier member comprises an epithelial neogenesis compatible material.

4. The implantable infection barrier seal as claimed in claim 1, wherein said implantable infection barrier member comprises calcium hydroxy-apatite.

5. The implantable infection barrier seal as claimed in claim 1, wherein said tissues are connective tissues comprising bone, and wherein said implantable infection barrier member is bondable to said bone, thereby providing said shield.

6. The implantable infection barrier seal as claimed in claim 1, wherein said tissues are connective tissues comprise an epithelium layer, and wherein said implantable infection barrier member is bondable to said epithelium layer, thereby providing said shield.

7. The implantable infection barrier seal as claimed in claim 5 or 6, wherein said implantable infection barrier member comprises an osteogenesis compatible material.

8. The implantable infection barrier seal as claimed in claim 7, wherein said implantable infection barrier member comprises calcium hydroxy-apatite.

9. The implantable infection barrier seal as claimed in claim 5 or 6, wherein said implantable infection barrier member comprises an epithelial neogenesis compatible material.

10. The implantable infection barrier seal as claimed in claim 9, wherein said implantable infection barrier member comprises a ceramic material.

11. The implantable infection barrier seal as claimed in claim 10, wherein said implantable infection barrier member comprises calcium hydroxy-apatite.

12. An implantable infection barrier seal for preventing the entry of pathogens into an anatomical body, said body defining an exterior where pathogens reside and an interior where pathogens are not endemic, said body interior including a cochlea that has an orifice, said orifice having a bone portion, and an elongated intracochlear implant having one end adapted to be positioned inside said cochlea and another end exposed to said exterior, comprising
an implantable infection barrier member shaped to fit within said orifice and comprising an inert, biologically compatible material, said barrier member being bonded to said implant and capable of being bonded to said bone portion so as to form a shield between said cochlea and said body exterior, thereby preventing the entry of said pathogens into said cochlea.

13. The implantable infection barrier seal as claimed in claim 12, wherein said cochlear orifice further includes an epithelium layer that is positioned adjacent said portion, and wherein said implantable infection barrier member is bondable to said epithelium layer, thereby providing an additional barrier to said pathogens.

14. The implantable infection barrier seal as claimed in claim 12 or 13, wherein said implantable infection barrier member is generally annular and has an inner perimeter that is bonded to said implant and an outer perimeter that is bondable to both said bone portion and said epithelium layer.

15. The implantable infection barrier seal as claimed in claim 14, wherein said implantable infection barrier member comprises an osteogenesis compatible material.

16. The implantable infection barrier seal as claimed in claim 15, wherein said implantable infection barrier member comprises an epithelial neogenesis compatible material.

17. The implantable infection barrier seal as claimed in claim 16, wherein said implantable infection barrier member comprises a porous ceramic material having a pore size in the range of from 50 to 400 micrometers.

18. The implantable infection barrier seal as claimed in claim 17, wherein said implantable infection barrier member comprises calcium hydroxy-apatite.

19. The implantable infection barrier seal as claimed in claim 18, further comprising
means comprising a paste-like composition of chips of said bone portion for enhancing said bonding of said implantable infection barrier member to said bone portion.

20. A method of creating an implantable infection barrier seal to prevent the entry of pathogens into an anatomical body, said body defining an exterior where pathogens reside and an interior where pathogens are not endemic, said body interior including organic tissues which are not inherently exposed to said exterior, comprising
exposing a portion of said tissues to said exterior,
preparing said tissue portion with an opening shaped to receive said implantable infection barrier seal,
forming said implantable infection barrier seal to include an implantable infection barrier member that comprises an inert, biologically compatible material which is capable of fitting within said opening and bonding to said exposed tissue portion directly, wherein said implantable infection barrier member comprises a porous ceramic material having a pore size in the range of from 50 to 400 micrometers and
positioning said implantable infection barrier member adjacent to said exposed tissue portion so as to bond said member to said exposed tissue portion directly, thereby shielding said body interior from said pathogens residing in said exterior.

21. The method as claimed in claim 20, wherein said implantable infection barrier member comprises an osteogenesis compatible material.

22. The method as claimed in claim 20, wherein said implantable infection barrier member comprises an epithelial neogenesis compatible material.

23. The method as claimed in 20, wherein said implantable infection barrier member comprises calcium hydroxy-apatite.

24. A method of creating an implantable infection barrier seal to prevent the entry of pathogens into an anatomical body, said body defining an exterior where pathogens reside and an interior where pathogens are not endemic, said body interior including a cochlea that has an orifice, said orifice having a bone portion, said orifice being adapted to receive an elongated intracochlear implant one end of which is positioned inside said cochlea and another end which is exposed to said exterior, comprising
exposing a portion of said orifice to said exterior,
preparing said exposed orifice portion to receive said implantable infection barrier seal,
providing said implantable infection barrier seal, said seal including an implantable infection barrier member that comprises of an inert, biologically compatible material which is capable of bonding to said exposed orifice portion, to provide a shield between said cochlea and said body exterior, and positioning said implantable infection barrier member adjacent to said exposed orifice portion so as to enhance said bonding of said member with said exposed orifice portion, thereby shielding said cochlea from said pathogens residing in said exterior.

25. The method as claimed in claim 24, wherein said cochlear orifice further includes an epithelium layer that is positioned adjacent said bone portion, and wherein said implantable infection barrier member is bonded to said epithelium layer, thereby providing an additional barrier to said pathogens.

26. The method as claimed in claim 24 or 25, wherein said implantable infection barrier member is a generally annular device having an inner perimeter that is bonded to said elogated implant and an outer perimeter that is bonded to both said bone portion and said epithelium layer.

27. The method as claimed in claim 26, wherein said implantable infection barrier member comprises an osteogenesis compatible material.

28. The method as claimed in claim 27, wherein said implantable infection barrier member comprises an epithelial neogenesis compatible material.

29. The method as claimed in claim 28, wherein said implantable infection barrier member comprises a ceramic material.

30. The method as claimed in claim 29, wherein said implantable infection barrier member comprises calcium hydroxy-apatite.

31. The method as claimed in claim 30, further comprising
providing a paste-like composition of chips of said bone portion to enhance said bonding of said implantable infection barrier member with said bone portion, and
positioning said composition contiguous with said member to as to enhance said bonding.

* * * * *